(12) United States Patent
Chang

(10) Patent No.: US 11,648,144 B2
(45) Date of Patent: May 16, 2023

(54) DEVICE FOR CORRECTING FORWARD HEAD POSTURE

(71) Applicant: Ki Yong Chang, Seoul (KR)

(72) Inventor: Ki Yong Chang, Seoul (KR)

( * ) Notice: Subject to any disclaimer, the term of this patent is extended or adjusted under 35 U.S.C. 154(b) by 22 days.

(21) Appl. No.: 17/061,774

(22) Filed: Oct. 2, 2020

(65) Prior Publication Data

US 2021/0121316 A1    Apr. 29, 2021

(30) Foreign Application Priority Data

Oct. 28, 2019    (KR) ........................ 10-2019-0134683

(51) Int. Cl.
*A61F 5/37* (2006.01)
*A61F 5/01* (2006.01)

(52) U.S. Cl.
CPC .......... *A61F 5/3707* (2013.01); *A61F 5/0102* (2013.01); *A61F 2005/0167* (2013.01)

(58) Field of Classification Search
CPC .. A61F 5/37; A61F 5/3707; A61F 5/00; A61F 5/01; A61F 5/055; A61F 5/058; A61F 5/05883; A61F 5/05891; A61F 5/102; A61F 2005/0132; A61F 2005/0165; A61F 2005/0167; A61F 5/02; A61F 5/0118; A61G 13/12; A61G 13/1205; A61G 13/121; A61H 1/0218; A61H 1/0296; A61H 2201/1611; A61H 2205/04; A45F 5/021
See application file for complete search history.

(56) References Cited

U.S. PATENT DOCUMENTS

| | | | |
|---|---|---|---|
| 5,964,722 A | | 10/1999 | Goralnik et al. |
| 6,503,213 B2 * | | 1/2003 | Bonutti ...................... A61F 5/02 |
| | | | 602/5 |
| 2009/0149788 A1 * | | 6/2009 | Dellanno ................ A61F 5/055 |
| | | | 602/18 |
| 2017/0127767 A1 * | | 5/2017 | Paik ........................ A45F 5/021 |
| 2017/0281390 A1 * | | 10/2017 | Abdul-Hafiz ......... A61F 5/0118 |

FOREIGN PATENT DOCUMENTS

| | | | |
|---|---|---|---|
| CN | 204971737 U | | 1/2016 |
| CN | 108125741 A | | 6/2018 |
| CN | 109210353 A | | 1/2019 |
| KR | 10-1559109 | | 10/2015 |
| KR | 10-2018-0104836 | | 9/2018 |
| KR | 20190036883 A | * | 4/2019 |
| KR | 20190036883 A | * | 4/2019 |
| KR | 10-2019-0036883 | | 4/2020 |

OTHER PUBLICATIONS

Machine Translation of KR20190036883A, created 1/6/3022 from Espace.net (Year: 2019).*

* cited by examiner

*Primary Examiner* — Ophelia A Hawthorne
*Assistant Examiner* — Gina McCarthy
(74) *Attorney, Agent, or Firm* — George McGuire

(57) ABSTRACT

A device for correcting a forward head posture includes a front support configured to support a jaw of a user, a rear support configured to support a rear side of a cervical spine of the user, and an adjuster configured to adjust a distance between the front support and the rear support. As the adjuster is adjusted or operated, a lower jaw joint of the jaw of the user moves backward in a horizontal direction.

11 Claims, 10 Drawing Sheets

DEVICE FOR CORRECTING FORWARD HEAD POSTURE

CROSS-REFERENCE TO RELATED APPLICATION(S)

This application claims the benefit under 35 USC § 119(a) of Korean Patent Application No. 10-2019-0134683 filed on Oct. 28, 2019, in the Korean Intellectual Property Office, the entire disclosure of which is incorporated herein by reference for all purposes.

BACKGROUND

1. Field

One or more example embodiments relate to a device for correcting a forward head posture (FHP).

2. Description of Related Art

A normal cervical spine of the neck is curved to appropriately distribute the weight of a head and support the head. However, for office workers and students who have a sedentary lifestyle, working or studying in a sedentary posture for a protracted period of time, the head leans forwards from a centerline of the shoulder and the weight of the head is inclined forward, and thus the curve of the cervical spine stretches straightly and muscles of the neck and shoulder support the whole weight of the head. When such a sedentary posture continues, the cervical spine and the muscles are strained, and thus the curve of the cervical spine is straightened, which results in symptoms of a forward head posture (FHP). The symptoms include, for example, pains from the neck being stiff and the shoulder being sore and tense, tensional headaches, chronic fatigue, and difficulty in concentration, and the like. When these symptoms are ignored or neglected, a cervical disc in the neck is stimulated and may thus be herniated.

The above description has been possessed or acquired by the inventor(s) in the course of conceiving the present disclosure and is not necessarily an art publicly known before the present application is filed.

SUMMARY

According to an example embodiment, there is provided a device for correcting a forward head posture (FHP) including a front support configured to support a jaw of a user, a rear support configured to support a rear side of a cervical spine of the user, and an adjuster configured to adjust a distance between the front support and the rear support. As the adjuster is adjusted, a lower jaw joint of the jaw of the user may move backward in a horizontal direction.

The adjuster may include an adjustment frame configured to be fixed to one of the front support and the rear support, a pair of sliding frames configured to slide in the adjustment frame to be connected to the other one of the front support and the rear support, and an adjustment handle configured to rotate on the adjustment frame and transfer a rotational force that slides the sliding frames in opposite directions to each other.

The pair of the sliding frames and the adjustment handle may be engaged with each other as a rack and pinion structure. The sliding frames may slide by the same length in response to a rotation angle of the adjustment handle.

The adjustment frame may include an adjustment handle receiver configured to receive therein at least a portion of the adjustment handle, and a ratchet member formed on an inner circumferential surface of the adjustment handle receiver. The adjustment handle may include a stopper configured to restrict a rotation direction of the adjustment handle by being combined with the ratchet member in shape.

The adjustment handle may further include a rotating body configured to be rotatably fixed to the front support. The stopper may be formed integrally with the rotating body and configured to be elastically deformed in a direction receding from a center of the rotating body.

The adjustment handle may include a grip portion by which the user grabs and configured to relatively rotate with respect to the rotating body, and an operating protrusion protruding from the grip portion and configured to press the stopper to allow the stopper to be closer to the center of the rotating body based on a relative rotation angle of the grip portion and the rotating body.

The adjuster may include a connecting band configured to be connected to one of the front support and the rear support, a pair of fastening members formed on both sides of the connecting band, and the pair of the sliding frames each including a head configured to be fastened to each of the fastening members.

Each of the fastening members may include a recess portion recessed in a first direction to receive therein the head, and a fastening groove recessed in a second direction perpendicular to the first direction from the recess portion. The head may include a wing portion configured to be inserted into the fastening groove. When the head slides to be fastened to a corresponding fastening member in the second direction after being received in the fastening member in the first direction, the wing portion may be fastened to the fastening groove to prevent the head from deviating from the fastening member in the first direction.

Each of the fastening members may further include a fastening member magnet disposed in the recess portion. The head further may further include a head magnet configured to be connected to the fastening member magnet through magnetism.

A distance from the wing portion to a center of the head magnet may be the same as a distance from the fastening groove to a center of the fastening member magnet.

A length of the head may be less than a length of the recess portion based on the second direction.

The front support may include a jaw supporting frame protruding from the front support toward a center of the device, and a front extension frame configured to support an upper body of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

Figure 1:
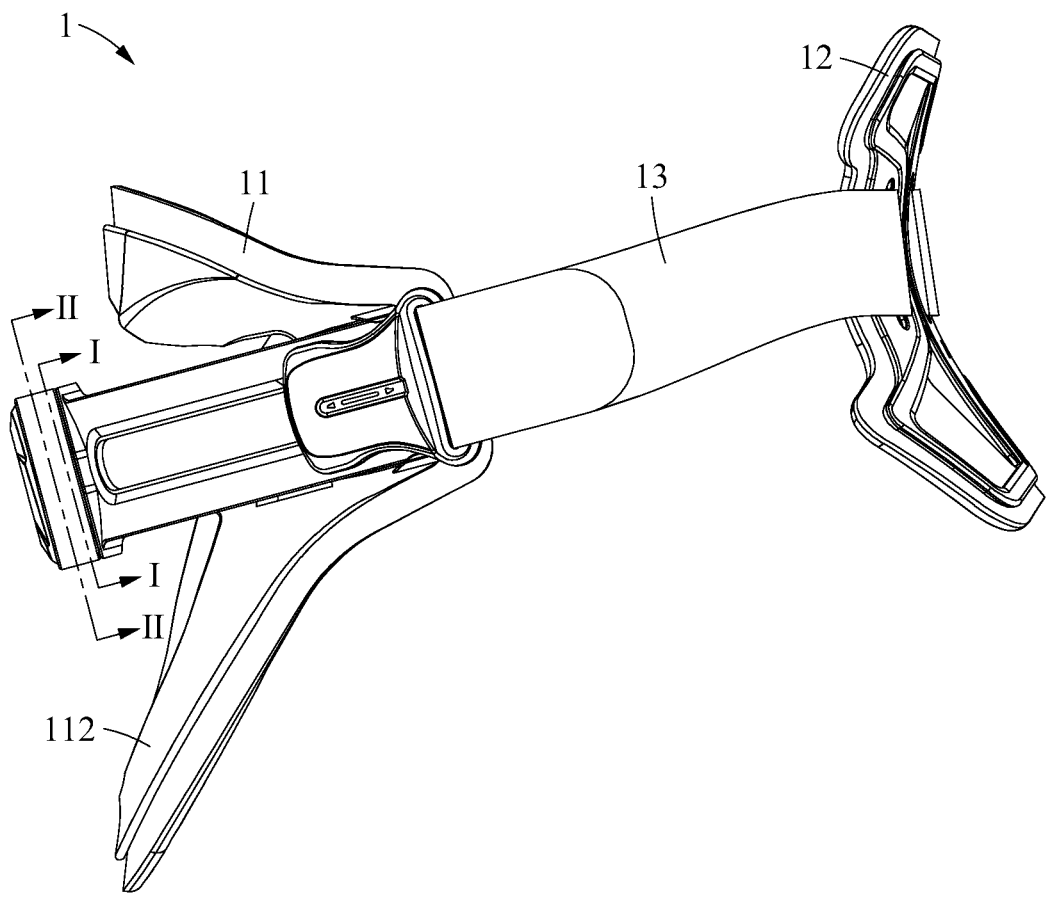
FIG. 1 is a side elevation view of a forward head posture (FHP) correcting device according to an example embodiment.

Hereinafter, example embodiments will be described in detail with reference to the accompanying drawings. It should be understood, however, that there is no intent to limit this disclosure to the particular example embodiments disclosed. On the contrary, example embodiments are to cover all modifications, equivalents, and alternatives falling within the scope of the example embodiments.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. In addition, terms such as first, second, A, B, (a), (b), and the like may be used herein to describe components. Each of these terminologies is not used to define an essence, order, or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

Hereinafter, example embodiments will be described in detail with reference to the accompanying drawings. In the description of example embodiments, detailed description of well-known related structures or functions will be omitted when it is deemed that such description will cause ambiguous interpretation of the present disclosure. Regarding the reference numerals assigned to the elements in the drawings, it should be noted that the same elements will be designated by the same reference numerals, wherever possible, even though they are shown in different drawings.

Figure 2:
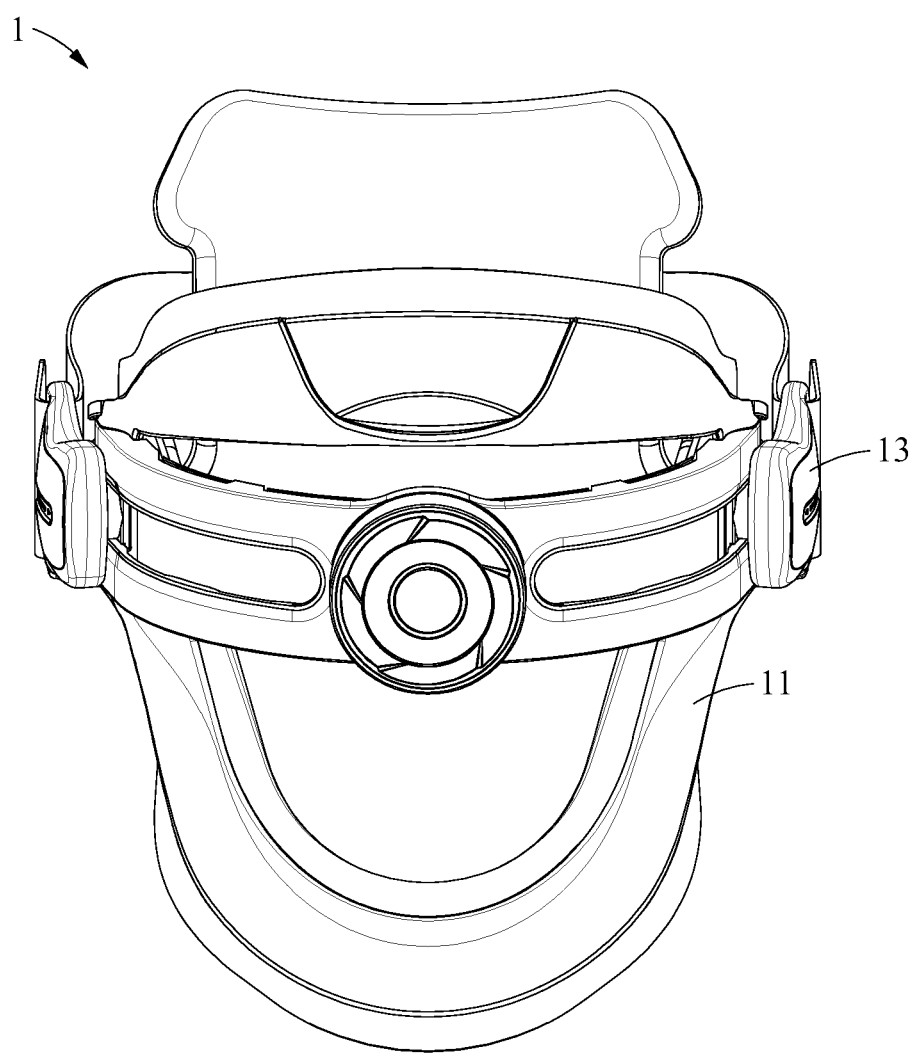
FIG. 2 is a front elevation view of an FHP correcting device according to an example embodiment.
Figure 3:
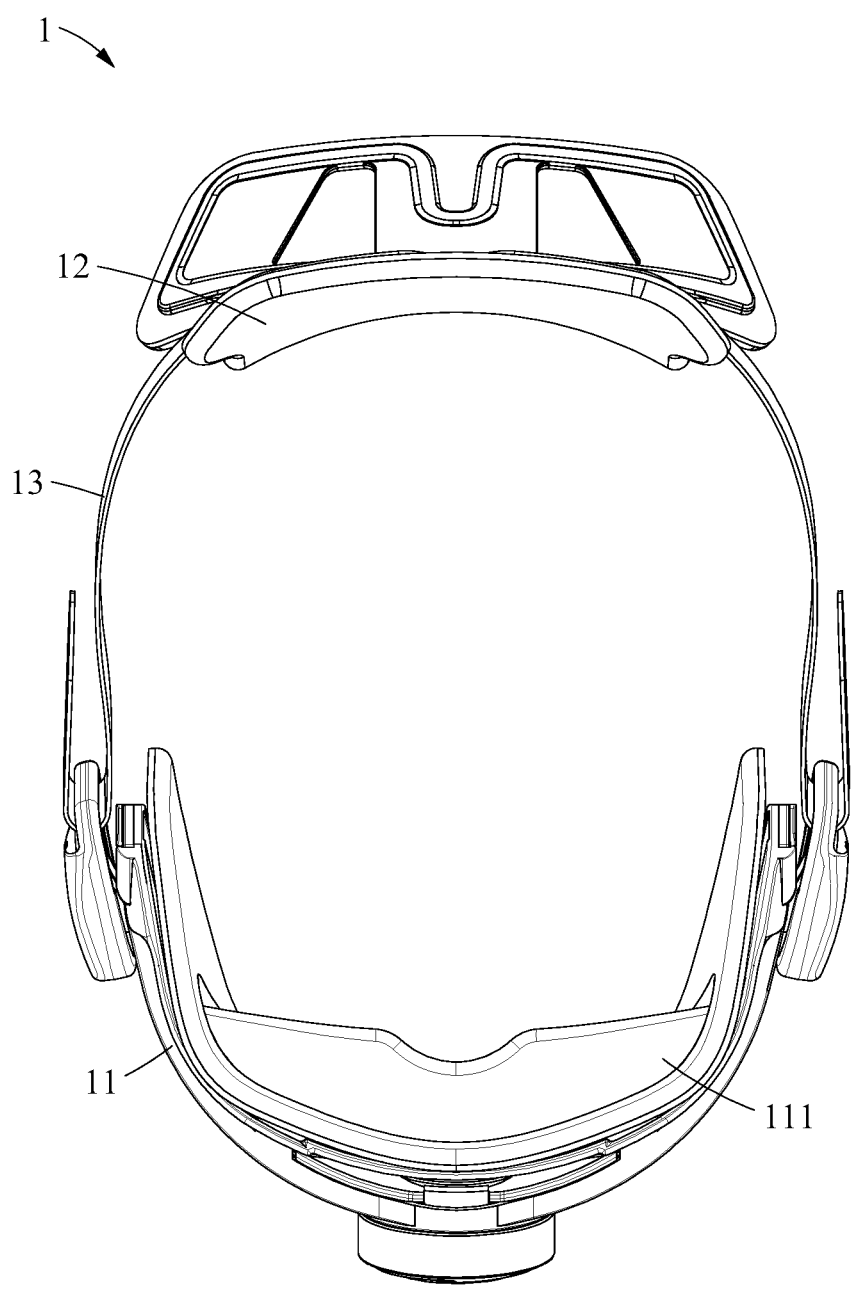
FIG. 3 is a top view of an FHP correcting device according to an example embodiment.

FIG. 1 is a side elevation view of a forward head posture (FHP) correcting device according to an example embodiment. FIG. 2 is a front elevation view of an FHP correcting device according to an example embodiment. FIG. 3 is a top view of an FHP correcting device according to an example embodiment.

Referring to FIGS. 1 through 3, an FHP correcting device 1 may move a lower jaw joint of a jaw of a user in a horizontal direction while supporting the jaw of the user and a rear side of a cervical spine of a neck of the user. For example, the FHP correcting device 1 may not simply prevent a movement of the neck, but move the jaw backward in the horizontal direction to provide a suitable stimulus to all seven cervical vertebrae in the neck of the user, thereby correcting the cervical vertebrae to be in a curved form. The FHP correcting device 1 includes a front support 11, a rear support 12, and an adjuster 13.

The front support 11 supports the jaw of the user. For example, the front support 11 comes in contact with a front side of the jaw of the user and provides a force for correcting an FHP. The front support 11 includes a jaw supporting frame 111 and a front extension frame 112.

The jaw supporting frame 111 protrudes from the front support 11 toward a center of the FHP correcting device 1. Thus, an inner side surface of the front support 11 and an upper side surface of the jaw supporting frame 11 roughly form an L shape, and thus may press the jaw of the user backward while stably surrounding a front portion and a rear portion of the jaw of the user. For example, the jaw supporting frame 111 comes in contact with a lower portion of the jaw of the user such that a head of the user faces forward, inducing the user to take a posture required to correct an FHP.

The front extension frame 112 supports an upper body of the user. For example, based on a shape of the FHP correcting device 1 worn on the user, the front extension frame 112 extends forward and downward from the jaw supporting frame 111, and may thus support a chest of the user from a front side. The front extension frame 112 maintains a distance between the head and the chest of the user, inducing the user to take a posture required to correct an FHP.

The rear support 12 supports the rear side of the cervical spine of the user. For example, the rear support 12 is provided in a curved form which corresponds to a normal form of the cervical spine. That is, based on the shape of the FHP correcting device 1 worn on the user, a center portion of the rear support 12 is curved forward, facing toward the user, compared to an upper end portion and a lower end portion thereof. Thus, it is possible to provide an appropriate stimulus to C3 and C4 segments of the seven cervical vertebrae that are not easy to be stimulated by a general manipulation or operation, and thus effectively correct an FHP.

The adjuster 13 adjusts a distance between the front support 11 and the rear support 12. For example, by adjusting the adjuster 13 to decrease this distance, it is possible to move the lower jaw of the user backward in the horizontal direction. Such an operation of the FHP correcting device 1 may provide the cervical spine of the user with the same stimulus as one that is provided by kinesiotherapy conducted using a manual force of human hands to correct an FHP. Thus, the user may continue to do exercise for correcting an FHP with his/her hands free while doing daily routines or working at the office.

Figure 4:
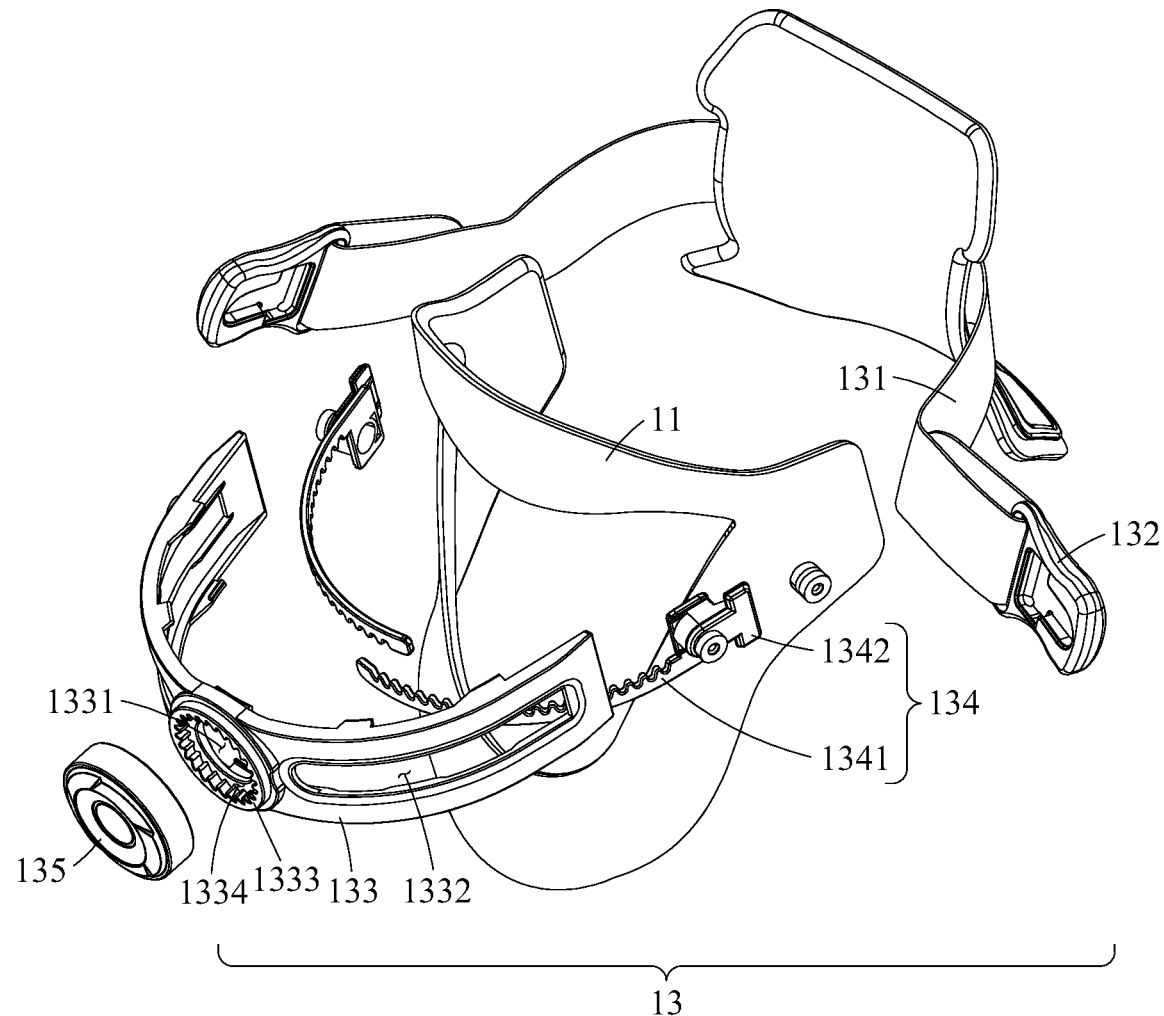
FIG. 4 is an exploded perspective view of an adjuster according to an example embodiment.

FIG. 4 is an exploded perspective view of an adjuster according to an example embodiment.

Referring to FIG. 4, the adjuster 13 includes a connecting band 131, a pair of fastening members 132, an adjustment frame 133, a pair of sliding frames 134, and an adjustment handle 135.

The connecting band 131 is connected to at least one of the front support 11 or the rear support 12. The connecting band 131 is formed with an elastic material, for example. Thus, the connecting band 131 may allow the user to move even when the user wears the FHP correcting device 1 of FIG. 1, and thus allow the user to feel comfortable even with the FHP correcting device 1 being worn on the user for a long period of time.

The adjustment frame 133 is fixed to one of the front support 11 and the rear support 12. FIG. 4 illustrates an example of the adjustment frame 133 being fixed to the front support 11. The adjustment frame 133 defines a circumference of the FHP correcting device 1 along with the connecting band 131. Although the adjustment frame 133 is illustrated as being fixed to the front support 11 in FIGS. 1 through 4, the adjustment frame 133 may be fixed to the rear support 12. The adjustment frame 133 includes an adjustment handle receiver 1331, a sliding frame receiver 1332, a ratchet member 1333, and a stepped portion 1334.

The pair of the fastening members 132 is formed on both sides of the connecting band 131. For example, the pair of the fastening members 132 may be a medium that connects the adjustment frame 133 to the connecting band 131.

The pair of the sliding frames 134 slides inside the adjustment frame 133. When the adjustment frame 133 is fixed to the front support 11 as illustrated in FIG. 4, the pair of the sliding frames 134 may be connected to the rear support 12. For example, as illustrated, the pair of the sliding frames 134 may be indirectly connected to the rear support 12 through the pair of the fastening members 132 and the connecting band 131. However, it is also possible that the pair of the sliding frames 134 is directly connected to the rear support 12.

However, when the adjustment frame 133 is fixed to the rear support 12 unlike what is illustrated in FIG. 4, the pair of the sliding frames 134 may be connected to the front support 11. That is, the adjustment frame 133 may be fixed to one of the front support 11 and the rear support 12, and the pair of the sliding frames 134 may be connected to the other one of the front support 11 and the rear support 12.

The pair of the sliding frames 134 slides in the adjustment frame 133, and determines a position in the adjustment frame 133 at which the connecting band 131 is to be fastened. By adjusting the position, it is possible to increase or decrease the circumference of the FHP correcting device 1. Each of the sliding frames 134 includes a rack member 1341 and a head 1342.

The adjustment handle 135 rotates on the adjustment frame 133 and transfers a rotational force that slides the sliding frames 134 in opposite directions to each other.

That the connecting band 131, the adjustment frame 133, and the pair of the sliding frames 134 are connected to either one of the front support 11 or the rear support 12 may be construed as including a direct connection to a support and also an indirect connection to the support through a band. When the adjustment frame 133 and the pair of the sliding frames 134 are connected to the front support 11 as illustrated, the user may operate or adjust it from the front, and thus the operation or adjustment may be performed more readily and conveniently.

Figure 5:
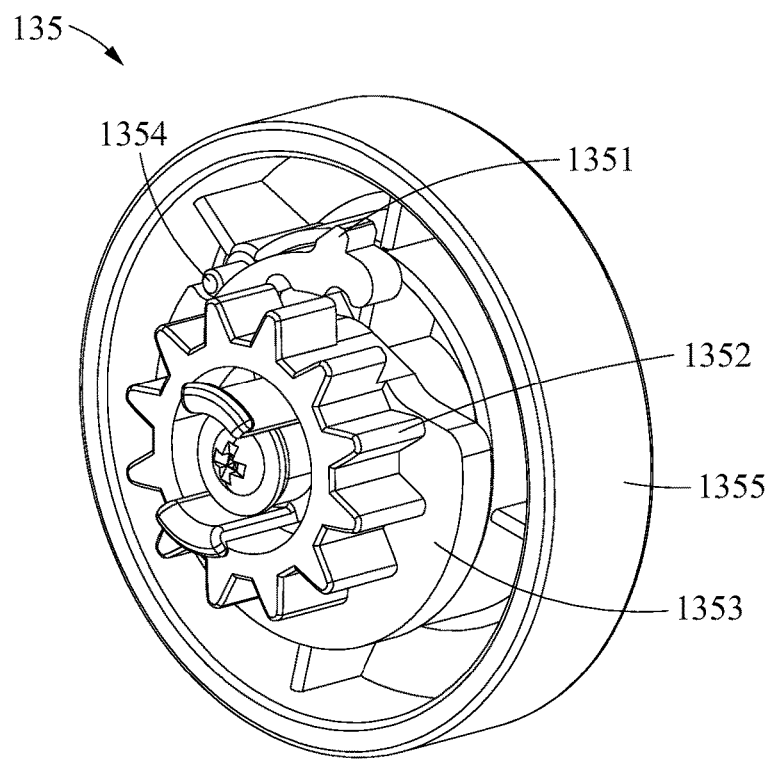
FIG. 5 is a perspective view of an adjustment handle according to an example embodiment.

FIG. 5 is a perspective view of an adjustment handle according to an example embodiment.

Referring to FIG. 5, the adjustment handle 135 includes a stopper 1351, a pinion member 1352, a rotating body 1353, an operating protrusion 1354, and a grip portion 1355.

The stopper 1351 is combined with the ratchet member 1333 in shape (refer to FIG. 8), and thus restricts a rotation direction of the adjustment handle 135. In addition, the stopper 1351 is integrally formed with the rotating body 1353 and elastically deformed toward a direction receding farther from a center of the rotating body 1353. For example, as illustrated, the stopper 1351 may be provided in a shape having a sufficiently small cross-sectional area and extending long from the rotating body 1353 such that the stopper 1351 is flexible. When an external force is applied, the stopper 1351 is deformed in a direction toward the center of the rotating body 1353. When the external force is released, the stopper 1351 is elastically deformed in the direction receding from the center of the rotating body 1353 by resilience. For example, the rotating body 1353 and the stopper 1351 may be formed using the same material such as, for example, synthetic resin, through injection molding. Thus, it may not need to use, as an additional part, a spring that is generally formed with a metal material to provide elasticity, and it is thus possible to reduce the number of parts to be used and the number of assembling processes required.

The rotating body 1353 is rotatably fixed to the front support 11. For example, the rotating body 1353 rotates with respect to the front support 11 and the adjustment frame 133 while the adjustment handle 135 is accommodated in the adjustment frame 133. The rotating body 1353 is installed to be rotatable in a preset range with respect to the grip portion 1355.

The pinion member 1352 is integrally formed with the rotating body 1353 to rotate along with the rotating body 1353. For example, the pinion member 1352 is combined, in shape, with the rack member 1341 to be described hereinafter while the adjustment handle 135 is accommodated in the adjustment frame 133.

The operating protrusion 1354 protrudes from the grip portion 1355 while fixed to an inner side of the grip portion 1355. As the grip portion 1355 rotates, the operating protrusion 1354 moves toward the stopper 1351 and presses the stopper 1351 such that the stopper 1351 is closer to the center of the rotating body 1353.

The grip portion 1355 is a portion by which the user grabs, and is relatively rotatable with respect to the rotating body 1353. A relationship among respective operations of the operating protrusion 1354, the stopper 1351, and the rotating body 1353 by the rotation of the grip portion 1355 will be described in detail hereinafter.

Figure 6:
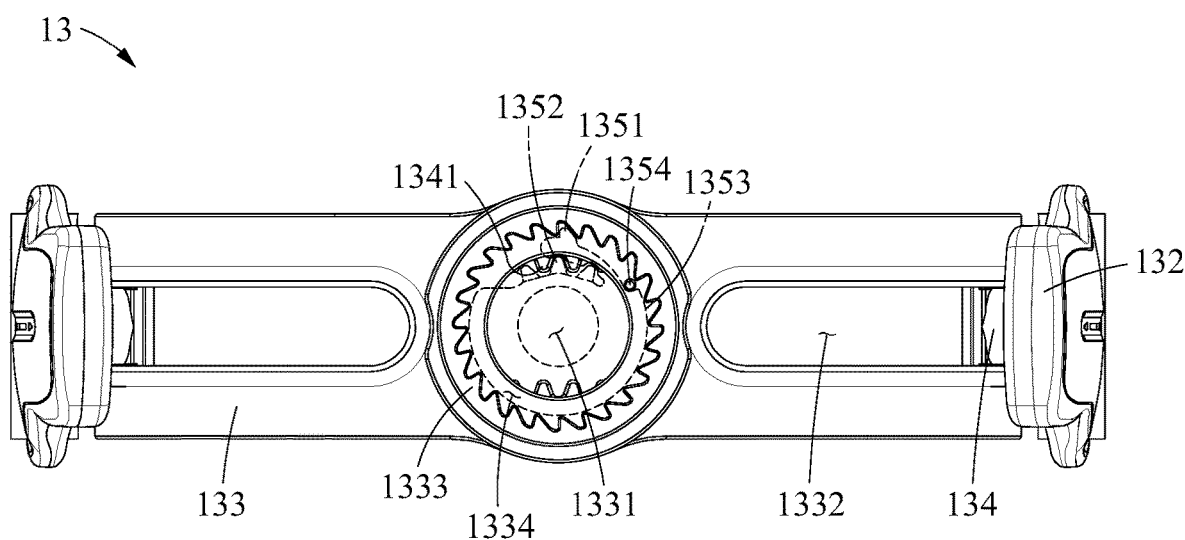
FIG. 6 is an elevation view of an adjustment frame according to an example embodiment.

FIG. 6 is an elevation view of an adjustment frame according to an example embodiment.

Referring to FIG. 6, the adjustment frame 133 includes the adjustment handle receiver 1331, the sliding frame receiver 1332, the ratchet member 1333, and the stepped portion 1334.

The adjustment handle receiver 1331 is formed as a portion of the adjustment frame 133 is perforated. The adjustment handle receiver 1331 provides a space that allows the adjustment handle 135 to be received in the adjustment frame 133, and thus allows the stopper 1351 and the pinion member 1352 of the adjustment handle 135 to interact with the ratchet member 1333 and the rack member 1341, respectively.

The sliding frame receiver 1332 receives a portion of the pair of the sliding frames 134, and is formed long in a longitudinal direction of the adjustment frame 133. For example, the pair of the sliding frames 134 and the pair of the fastening members 132 move along the sliding frame receiver 1332, and it is thus possible to adjust the circumference of the FHP correcting device 1 of FIG. 1.

The ratchet member 1333 is formed on an inner circumferential surface of the adjustment handle receiver 1331. The ratchet member 1333 is engaged with a portion of the stopper 1351 and may thus prevent the adjustment handle 135 from rotating further. For example, the ratchet member 1333 is provided in a shape slanted in one direction. That is, the ratchet member 1333 is provided in a shape in which a low slope (gentle slope) and a high slope (steep slope) are disposed alternately.

Figure 7:
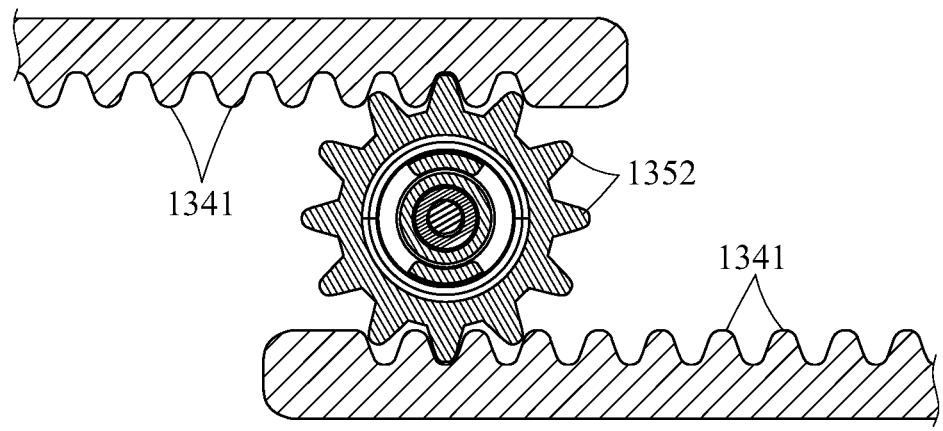
FIG. 7 is a cross-sectional view of the FHP correcting device cut by an I-I line of FIG. 1.

The stepped portion 1334 is a portion that supports the rotating body 1353 (refer to FIG. 5), and the pinion member 1352 is combined with the rack member 1341 by being inserted therein through a hole formed at a center of the stepped portion 1334 (refer to FIG. 7). Through this, even though the adjustment handle 135 (refer to FIG. 5) receives a force of pressing the adjustment frame 133 in a perpendicular direction, it is possible to prevent the force from hindering the rack member 1341 and the pinion member 1352 from rotating while being engaged with each other, and thus ensure structural stability.

FIG. 7 is a cross-sectional view of the FHP correcting device 1 cut by an I-I line of FIG. 1.

FIG. 7 illustrates a state in which the rack member 1341 of each of the sliding frames 134 (refer to FIG. 4) and the pinion member 1352 of the adjustment handle 135 (refer to FIG. 5) are combined. By the rack member 1341 and the pinion member 1352, the pair of the sliding members 134 and the adjustment handle 135 may be engaged in a rack and pinion structure. For example, the sliding frames 134 slide by the same length in response to a rotation angle of the adjustment handle 135. That is, tooth forms of the sliding frames 134 may have symmetrical sizes and distances. Through this, only with a simple operation of rotating the adjustment handle 135 without exerting any special effort, the user may move the front support 11 toward the rear support 12 in the horizontal direction without the front support 11 not being slanted leftward or rightward.

Figure 8:
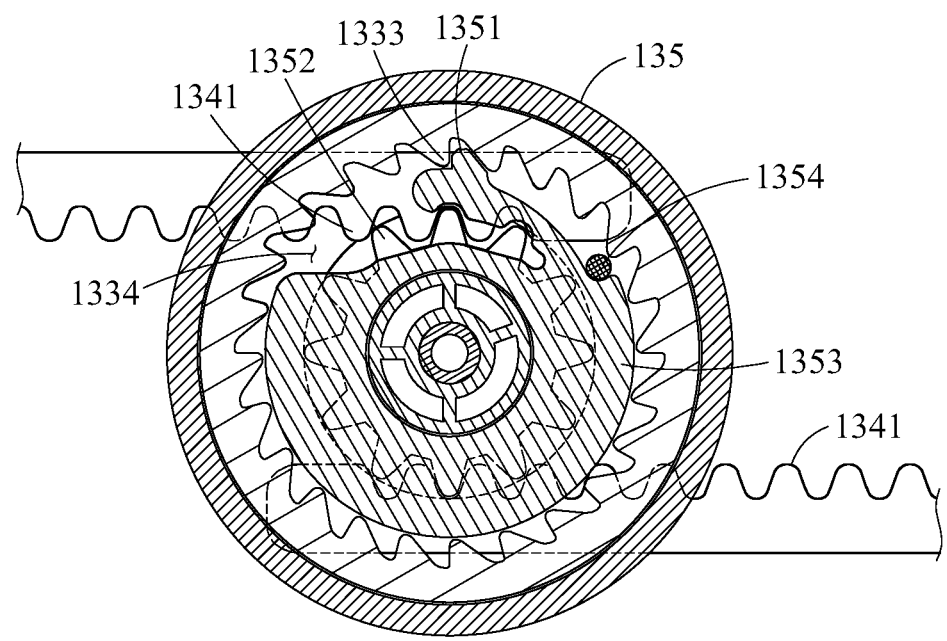
FIG. 8 is a cross-sectional view of the FHP correcting device cut by an II-II line of FIG. 1.

FIG. 8 is a cross-sectional view of the FHP correcting device 1 cut by an II-II line of FIG. 1.

FIG. 8 illustrates a state in which the stopper 1351 and the ratchet member 1333 are combined on the stepped portion 1334. The stopper 1351 is combined with the ratchet member 1333 in shape, thereby restricting a rotation direction of the adjustment handle 135.

For example, when the adjustment handle 135 rotates clockwise based on the state illustrated in FIG. 8, the stopper 1351 may smoothly move stepwise along low slopes. That is, the stopper 1351 may run over the low slopes of the ratchet member 1333, and thus pull a pair of ratchet members 1341 engaged with the pinion member 1352 while the pinion member 1352 is rotating clockwise along with the adjustment handle 134. Thus, a total circumferential length of the FHP correcting device 1 may decrease, and thus the front support 11 may move toward the rear support 12.

For another example, when the adjustment handle 135 rotates counterclockwise by a certain angle or less based on the state illustrated in FIG. 8, the stopper 1351 is combined in shape with respect to high slopes of the ratchet member 1333 and may not run over the high slopes, and the pinion member 1352 may not rotate. Thus, the total circumferential length of the FHP correcting device 1 may be maintained consistently.

In this example, while the adjustment handle 135 is rotating counterclockwise by the angle or less in the state illustrated in FIG. 8, the adjustment handle 135 may rotate idly, not transferring torque to the rotating body 1353. In addition, when the adjustment handle 135 rotates counterclockwise by an angle exceeding the angle, the operating protrusion 1354 may press the stopper 1351 to push the stopper 1351 toward the center of the rotating body 1353, and thus the stopper 1351 may be separated from the ratchet member 1333. Thus, the stopper 1351 may not be interfered with by the high slopes of the ratchet member 1333, and thus the adjustment handle 135 may rotate along with the rotating body 1353 to rotate the pinion member 1352 counterclockwise. In such a case, as the pinion member 1352 rotates along with the adjustment handle 135 counterclockwise, the pair of the rack members 1341 engaged with the pinion member 1352 may be separated farther to both sides, and thus the total circumferential length of the FHP correcting device 1 may increase and the front support 11 may move in a direction receding farther from the rear support 12.

Figure 9:
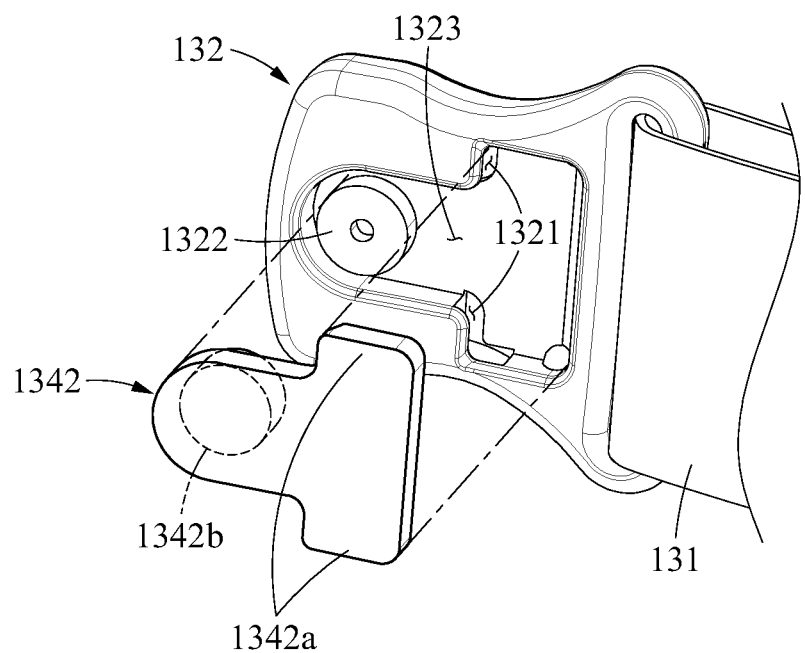
FIG. 9 is a perspective view of a fastening member and a head according to an example embodiment.

FIG. 9 is a perspective view of a fastening member and a head according to an example embodiment.

Referring to FIG. 9, each of the fastening members 132 includes a recess portion 1323, a fastening groove 1321, and a fastening member magnet 1322.

The recess portion 1323 is recessed in a first direction (a direction perpendicular to the ground based on FIG. 9) to receive therein the head 1342. For example, the recess portion 1323 may be recessed deeper than a thickness in the first direction of the head 1342 such that the head 1342 is completely received in a corresponding fastening member 132.

The fastening groove 1321 is recessed in a second direction (a left direction based on FIG. 9) that is perpendicular to the first direction from the recess portion 1323. For example, the fastening groove 1321 receives therein at least a portion of the head 1342 moving in the second direction.

The head 1342 passes through the adjustment frame 133 (refer to FIG. 4) to be connected to the fastening member 132. Based on the second direction, a length of the head 1342 may be less than a length of the recess portion 1323. The head 1342 includes a wing portion 1342a and a head magnet 1342b. A technical significance of such a structure will be described hereinafter with reference to FIG. 10.

The wing portion 1342a is inserted into the fastening groove 1321. In such a case, it is possible to prevent the fastening member 132 from deviating in the first direction.

The head magnet 1342b is connected to the fastening member magnet 1322 through magnetism. Through this, it is possible to prevent the fastening member 132 from deviating in the first direction or the second direction. A distance from the wing portion 1342a to a center of the head magnet 1342b may be the same as a distance from the fastening groove 1321 to a center of the fastening member magnet 1322. A technical significance of such a structure will be described hereinafter with reference to FIG. 10.

Figure 10:
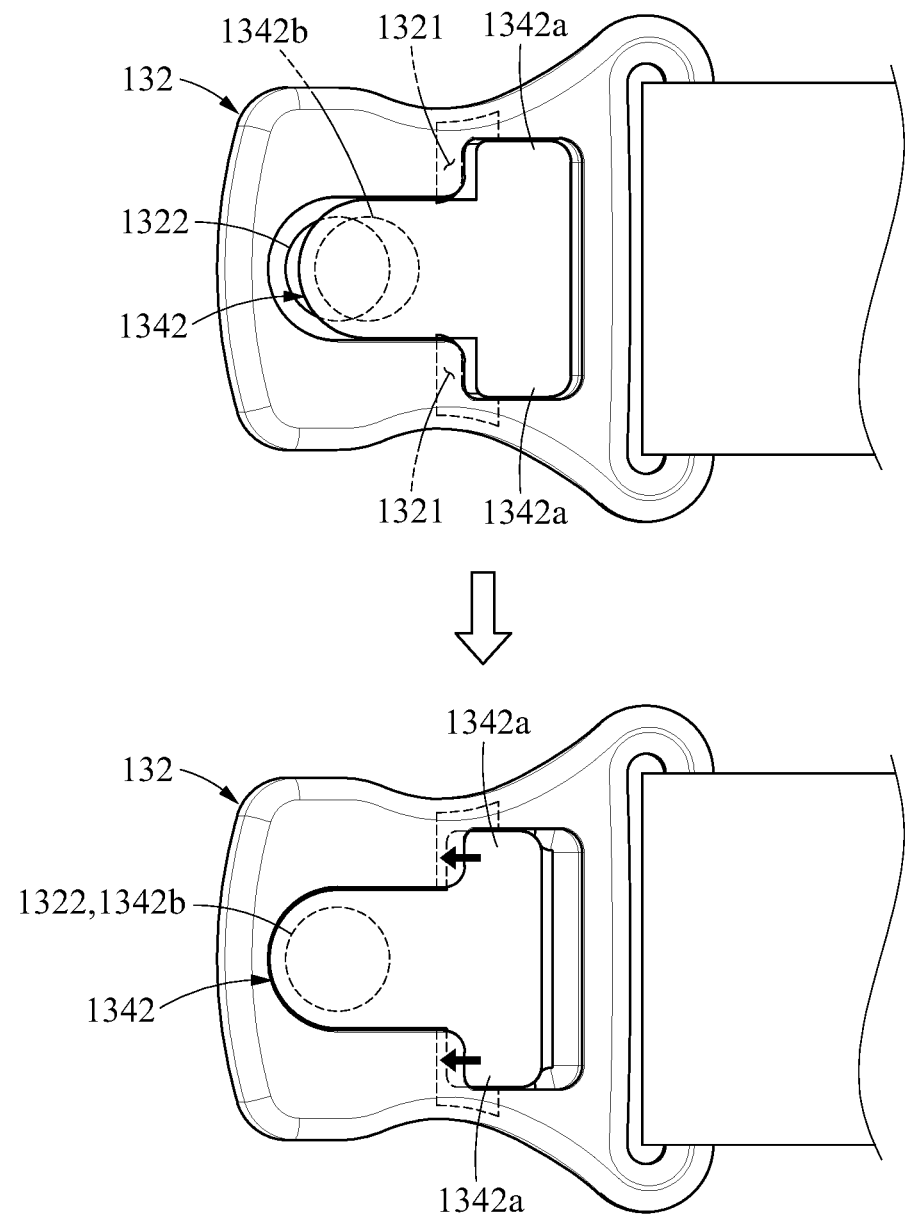
FIG. 10 illustrates how a fastening member and a head are fastened together according to an example embodiment.

FIG. 10 illustrates how a fastening member and a head are fastened together according to an example embodiment.

As illustrated in an upper portion of FIG. 10, the head 1342 is received inside the fastening member 132 in the first direction. Here, an attractive force may act between the fastening member magnet 1322 and the head magnet 1342b. In detail, the distance from the wing portion 1342a to the center of the head magnet 1342b may be the same as the distance from the fastening groove 1321 to the center of the fastening member magnet 1322, and the length of the head 1342 may be less than the length of the recess portion 1323 based on the second direction. Thus, while the head 1342 is accommodated in the first direction, the attractive force may act between the head magnet 1342*b* and the fastening member magnet 1322.

As illustrated in a lower portion of FIG. 10, the fastening member magnet 1322 pulls the head magnet 1342*b*, and the head 1342 slides to be fastened to the fastening member 132 in the second direction. In such a case, the wing portion 1342*a* is fastened to the fastening groove 1321, and it is thus possible to prevent the head 1342 from deviating from the fastening member 132 in the first direction.

That is, once the user puts the head 1342 into the fastening member 132 in the first direction, the head 1342 may move in the second direction by the attractive force between the fastening member magnet 1322 and the head magnet 1342*b*, and then be fastened thereto by itself.

Figure 11:
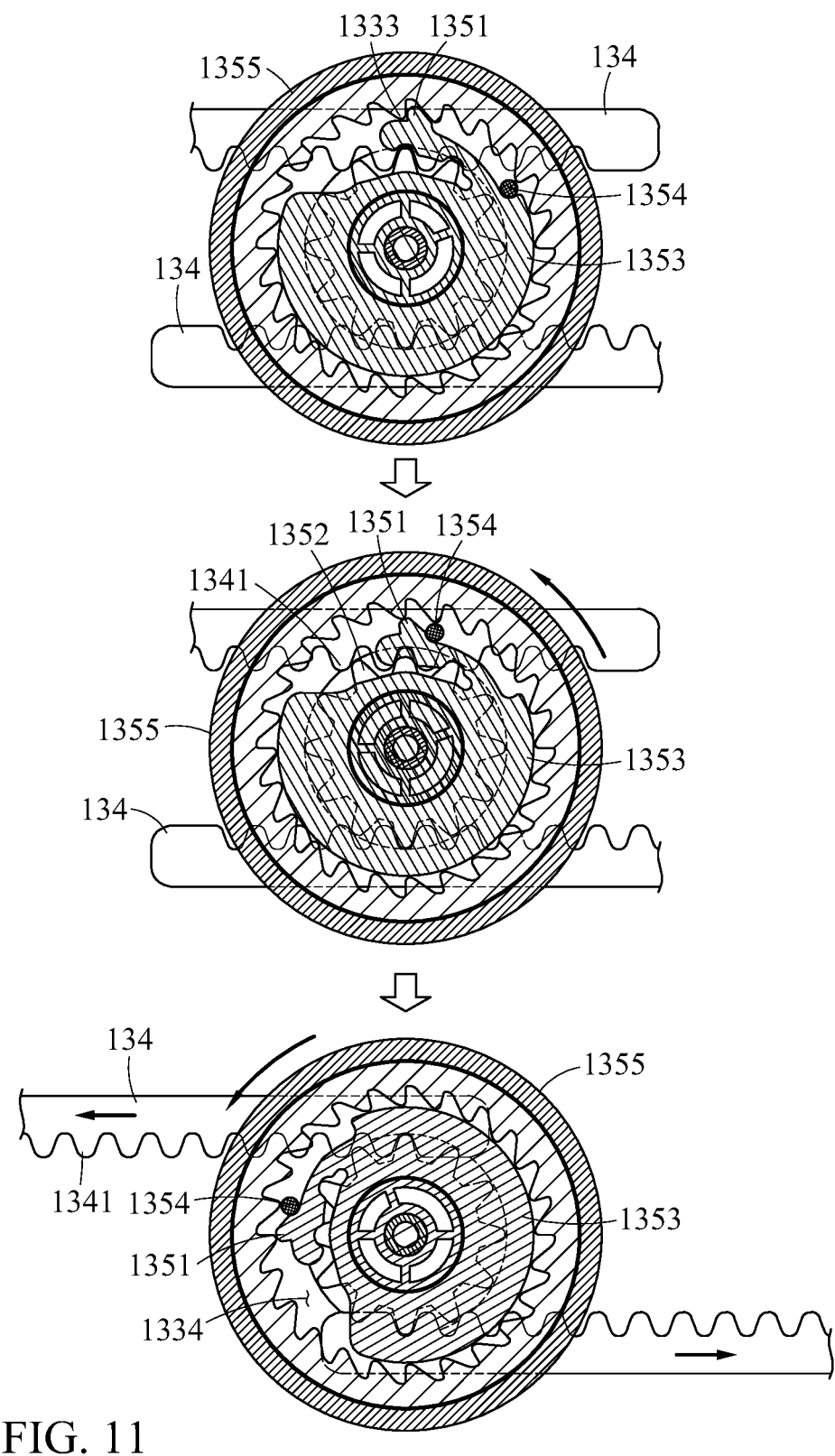
FIG. 11 illustrates an operation of increasing a circumference of an adjuster of an FHP correcting device according to an example embodiment.
Figure 12:
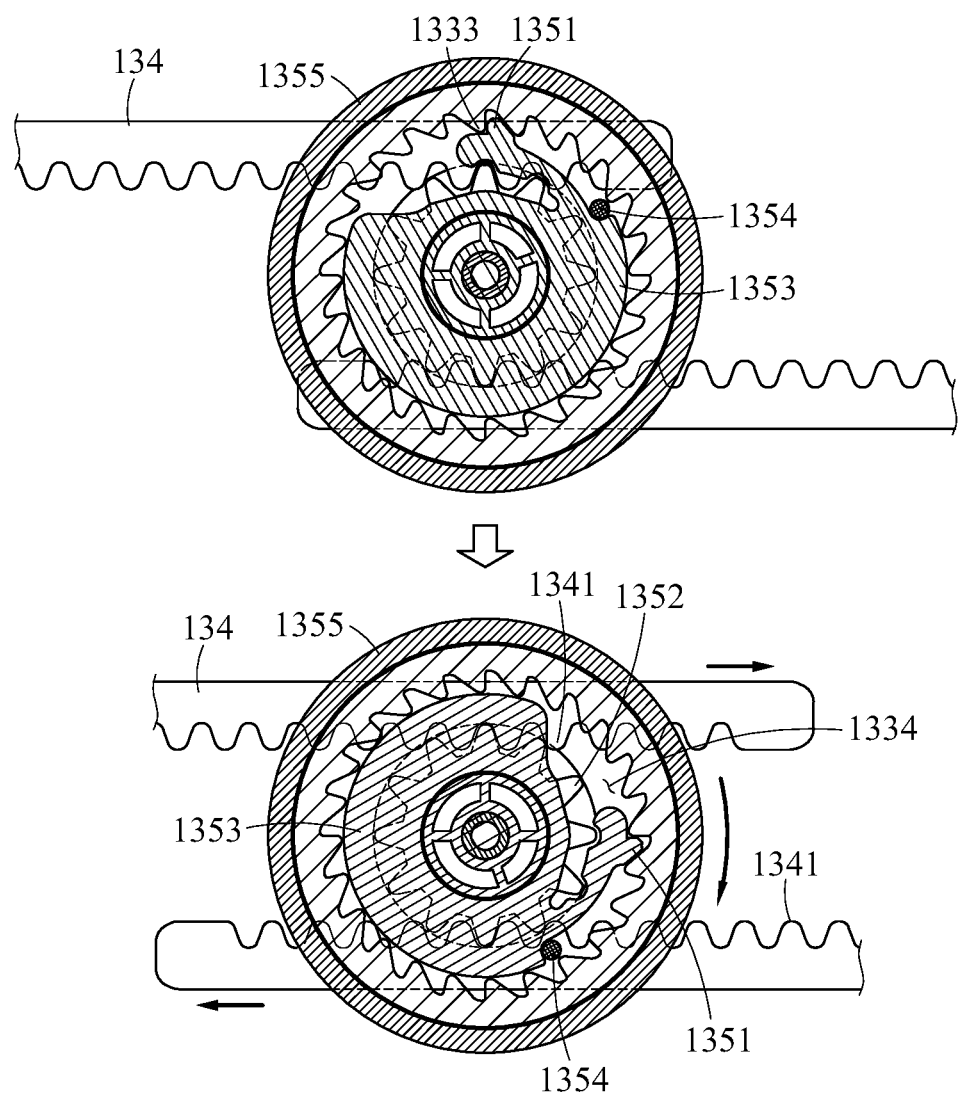
FIG. 12 illustrates an operation of decreasing a circumference of an adjuster of an FHP correcting device according to an example embodiment.

FIG. 11 illustrates an operation of increasing a circumference of an adjuster of an FHP correcting device according to an example embodiment. FIG. 12 illustrates an operation of decreasing a circumference of an adjuster of an FHP correcting device according to an example embodiment.

Referring to FIG. 11, when the grip portion 1355 rotates counterclockwise, the operating protrusion 1354 rotates counterclockwise with respect to the rotating body 1353 and the pair of the sliding frames 134. In this case, the stopper 1351 is combined in shape with a concave portion of the ratchet member 1333, and the pair of the sliding frames 134 does not move.

Subsequently, when the operating protrusion 1354 rotates further while being in contact with the stopper 1351, the operating protrusion 1354 presses the stopper 1351 and provides the stopper 1351 with an external force that acts in a direction toward the center of the rotating body 1353. In such a case, the stopper 1351 is separated from the ratchet member 1333.

Lastly, in a state in which the stopper 1351 is separated from the ratchet member 1333, the operating protrusion 1354, the grip portion 1355, and the rotating body 1353 rotate counterclockwise with respect to the ratchet member 1333 integrally and smoothly. When the rotating body 1353 rotates, the pinion member 1352 rotates, and thus the pair of the sliding frames 134 moves in a straight line, receding from each other, by the rotation of the pinion member 1352. Accordingly, the circumference of the FHP correcting device 1 of FIG. 1 may increase.

Referring to FIG. 12, when the grip portion 1355 rotates clockwise in a state illustrated in a middle portion of FIG. 11 or a lower portion of FIG. 11, the grip portion 1355 relatively rotates with respect to the rotating body 1353 (that is, the grip portion 1355 rotates idly), and the operating protrusion 1354 deviates from a state in which the operating protrusion 1354 presses the stopper 1351. In such a case, the stopper 1351 spreads in a direction receding from the center of the rotating body 1353 by an elastic restoring force (or resilience), and is combined in shape with the concave portion of the ratchet member 1333. When the grip portion 1355 rotates clockwise by a certain angle, the operating protrusion 1354 comes in contact with a fastening portion formed in the rotating body 1353 as illustrated in an upper portion of FIG. 12.

Subsequently, when the operating protrusion 1354 rotates further while being in contact with the rotating body 1353, the stopper 1351 moves one by one along the low slopes of the ratchet member 1333. As the stopper 1351 moves, the rotating body 1353 rotates clockwise. As the rotating body 1353 rotates, the pinion member 1352 also rotates. By the rotation of the pinion member 1352, a sliding frame 134 that is disposed on an upper side of the pair of the sliding frames 134 moves in a straight line rightward in a tangential direction, and a sliding frame 134 that is disposed on a lower side of the pair of the sliding frames 134 moves in a straight line leftward in a tangential direction. That is, as the grip portion 1355 rotates clockwise, the sliding frames 134 become closer to each other. Thus, the circumference of the FHP correcting device 1 of FIG. 1 may decrease.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A device for correcting a forward head posture, comprising:
   a front support configured to press against a front side of a jaw of the user and having a jaw supporting frame protruding from the front support toward a center of the device to contact a lower portion of the jaw of the user;
   a rear support configured to support a rear side of a cervical spine of the user; and
   an adjuster configured to adjust a distance between the front support and the rear support, wherein the adjuster includes an adjustment frame configured to be fixed to one of the front support and the rear support, a pair of sliding frames configured to slide in the adjustment frame to be connected to the other one of the front support and the rear support, and an adjustment handle configured to rotate on the adjustment frame and coupled to the pair of sliding frames so that rotation of the adjustment handle will cause the sliding frames to move in opposite directions to each other;
   wherein, as the adjuster is adjusted, the front support will cause a lower jaw joint of the jaw of the user to move backward in a horizontal direction.

2. The device of claim 1, wherein the adjuster comprises:
   a connecting band configured to be connected to one of the front support and the rear support;
   a pair of fastening members formed on both sides of the connecting band; and
   a pair of sliding frames comprising a head configured to be fastened to each of the fastening members.

3. The device of claim 2, wherein each of the fastening members comprises:
   a recess portion recessed in a first direction to receive therein the head; and
   a fastening groove recessed in a second direction perpendicular to the first direction from the recess portion,
   wherein the head comprises:
   a wing portion configured to be inserted into the fastening groove,
   wherein, when the head slides to be fastened to a corresponding fastening member in the second direction after being received in the fastening member in the first direction, the wing portion is configured to be fastened to the fastening groove to prevent the head from deviating from the fastening member in the first direction.

4. The device of claim 3, wherein each of the fastening members further comprises:

a fastening member magnet disposed in the recess portion, wherein the head further comprises:

a head magnet configured to be connected to the fastening member magnet through magnetism.

5. The device of claim 4, wherein a distance from the wing portion to a center of the head magnet is the same as a distance from the fastening groove to a center of the fastening member magnet.

6. The device of claim 5, wherein a length of the head is less than a length of the recess portion based on the second direction.

7. The device of claim 2, wherein the adjustment frame comprises:

an adjustment handle receiver configured to receive therein at least a portion of the adjustment handle; and a ratchet member formed on an inner circumferential surface of the adjustment handle receiver, wherein the adjustment handle comprises:

a stopper configured to restrict a rotation direction of the adjustment handle by being combined with the ratchet member in shape.

8. The device of claim 7, wherein the adjustment handle further comprises:

a rotating body configured to be rotatably fixed to the front support, wherein the stopper is formed integrally with the rotating body and configured to be elastically deformed in a direction receding from a center of the rotating body.

9. The device of claim 8, wherein the adjustment handle comprises:

a grip portion configured to be grabbed by the user and further configured to relatively rotate with respect to the rotating body; and an operating protrusion protruding from the grip portion and configured to press the stopper to allow the stopper to be closer to the center of the rotating body based on a relative rotation angle of the grip portion and the rotating body.

10. The device of claim 2, wherein the pair of the sliding frames and the adjustment handle are engaged with each other as a rack and pinion structure, wherein the sliding frames slide by the same length in response to a rotation angle of the adjustment handle.

11. The device of claim 1, wherein the front support further comprises a front extension frame configured to support an upper body of the user.

* * * * *